United States Patent
Tran et al.

(10) Patent No.: US 11,357,440 B2
(45) Date of Patent: Jun. 14, 2022

(54) INSERTABLE CARDIAC MONITORING DEVICE DESIGNED FOR THE MRI ENVIRONMENT

(71) Applicant: Cardiac Pacemakers, Inc., St. Paul, MN (US)

(72) Inventors: Binh C. Tran, Minneapolis, MN (US); Mitchell D. Lanz, Maple Grove, MN (US); Scott R. Vanderlinde, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 568 days.

(21) Appl. No.: 16/260,409

(22) Filed: Jan. 29, 2019

(65) Prior Publication Data
US 2019/0231206 A1    Aug. 1, 2019

Related U.S. Application Data

(60) Provisional application No. 62/625,092, filed on Feb. 1, 2018.

(51) Int. Cl.
*A61N 1/37* (2006.01)
*A61B 5/361* (2021.01)
(Continued)

(52) U.S. Cl.
CPC .............. *A61B 5/361* (2021.01); *A61B 5/283* (2021.01); *A61B 5/363* (2021.01); *A61B 5/686* (2013.01);
(Continued)

(58) Field of Classification Search
CPC ......... A61B 5/361; A61B 5/283; A61B 5/363; A61B 5/686; A61B 5/7282; A61B 5/055;
(Continued)

(56) References Cited

U.S. PATENT DOCUMENTS

| 6,937,906 B2 | 8/2005 | Terry et al. |
| 7,996,079 B2 | 8/2011 | Armstrong |

(Continued)

FOREIGN PATENT DOCUMENTS

| CN | 111918694 A | 11/2020 |
| WO | WO-2019152342 A1 | 8/2019 |

OTHER PUBLICATIONS

"European Application Serial No. 19707917.1, Response filed Mar. 9, 2021 to Communication pursuant to Rules 161(1) and 162 EPC dated Sep. 8, 2020", 20 pgs.

(Continued)

*Primary Examiner* — Eugene T Wu
(74) *Attorney, Agent, or Firm* — Schwegman Lundberg & Woessner, P.A.

(57) ABSTRACT

An apparatus comprises a magnetic field detection circuit, a cardiac signal sensing circuit, a memory circuit, a control circuit, and an arrhythmia detection circuit. The cardiac signal sensing circuit generates a cardiac signal representative of cardiac activity of a subject when coupled to sensing electrodes. The control circuit is operatively coupled to the magnetic field detection circuit; the cardiac signal sensing circuit, and the memory circuit. The control circuit stores cardiac signal data determined using the sensed cardiac signal, receives an indication of magnetic field detection by the magnetic field detection circuit, stores data obtained using the sensed cardiac signal during the magnetic field detection, and stores an identifier indicating the magnetic field detection in association with the data. The arrhythmia detection circuit processes the cardiac signal data to detect a cardiac arrhythmia event and confirm the cardiac arrhythmia event according to the magnetic field indication.

17 Claims, 3 Drawing Sheets

(51) Int. Cl.
  *A61N 1/05* (2006.01)
  *A61B 5/00* (2006.01)
  *A61B 5/283* (2021.01)
  *A61B 5/363* (2021.01)
  *A61N 1/39* (2006.01)
  *A61N 1/08* (2006.01)
  *A61B 5/055* (2006.01)

(52) U.S. Cl.
  CPC .......... *A61B 5/7282* (2013.01); *A61N 1/0504* (2013.01); *A61N 1/3718* (2013.01); *A61B 5/055* (2013.01); *A61B 5/6823* (2013.01); *A61B 2560/0247* (2013.01); *A61B 2562/0223* (2013.01); *A61N 1/08* (2013.01); *A61N 1/37* (2013.01); *A61N 1/3956* (2013.01)

(58) Field of Classification Search
  CPC .......... A61B 5/6823; A61B 2560/0247; A61B 2562/0223; A61N 1/0504; A61N 1/3718; A61N 1/08; A61N 1/37; A61N 1/3956
  See application file for complete search history.

(56) References Cited

U.S. PATENT DOCUMENTS

| | | | |
|---|---|---|---|
| 8,014,867 B2 | 9/2011 | Cooke et al. | |
| 8,121,678 B2 | 2/2012 | Linder et al. | |
| 8,140,159 B2 | 3/2012 | Inman et al. | |
| 8,165,693 B2 | 4/2012 | Inman et al. | |
| 8,180,462 B2 | 5/2012 | Inman et al. | |
| 8,373,556 B2 | 2/2013 | LaLonde et al. | |
| 8,437,853 B2 | 5/2013 | Inman et al. | |
| 8,515,547 B2 | 8/2013 | Mass et al. | |
| 8,521,300 B2 | 8/2013 | Makdissi | |
| 8,538,550 B2 | 9/2013 | Stubbs et al. | |
| 8,554,318 B2 | 10/2013 | Legay | |
| 8,583,255 B2 | 11/2013 | Legay | |
| 8,712,540 B2 | 4/2014 | Gadagkar et al. | |
| 8,755,886 B2 | 6/2014 | Stessman et al. | |
| 8,818,506 B2 | 8/2014 | Legay | |
| 8,849,413 B2 | 9/2014 | Makdissi | |
| 8,954,030 B1 | 2/2015 | Buchheit | |
| 9,031,652 B2 | 5/2015 | Hoyme et al. | |
| 9,101,781 B2 | 8/2015 | Legay | |
| 9,174,059 B2 | 11/2015 | Gadagkar et al. | |
| 9,265,960 B2 | 2/2016 | Hoyme et al. | |
| 9,272,152 B2 | 3/2016 | LaLonde et al. | |
| 9,278,212 B2 | 3/2016 | Makdissi | |
| 9,345,888 B2 | 5/2016 | Wedan et al. | |
| 9,411,027 B2 | 8/2016 | von Arx et al. | |
| 9,586,043 B2 | 3/2017 | LaLonde et al. | |
| 9,603,549 B2 | 3/2017 | Stubbs et al. | |
| 9,675,806 B2 | 6/2017 | Ellingson | |
| 9,694,188 B2 | 7/2017 | Gadagkar et al. | |
| 2011/0137359 A1* | 6/2011 | Stubbs ................... | A61N 1/056 607/4 |
| 2011/0156706 A1* | 6/2011 | Stubbs ................. | A61B 5/7203 324/318 |
| 2011/0160565 A1 | 6/2011 | Stubbs et al. | |
| 2011/0160567 A1 | 6/2011 | Stahmann et al. | |
| 2011/0160783 A1 | 6/2011 | Bocek et al. | |
| 2011/0187360 A1 | 8/2011 | Maile et al. | |
| 2012/0221068 A1 | 8/2012 | Ellingson | |
| 2012/0277817 A1 | 11/2012 | Ellingson et al. | |
| 2014/0058383 A1 | 2/2014 | Hoyme et al. | |
| 2014/0058468 A1 | 2/2014 | Hoyme et al. | |

OTHER PUBLICATIONS

"International Application Serial No. PCT/US2019/015523, International Preliminary Report on Patentability dated Aug. 13, 2020", 7 pgs.

"International Application Serial No. PCT/US2019/015523, International Search Report dated Apr. 12, 2019", 4 pgs.

"International Application Serial No. PCT/US2019/015523, Written Opinion dated Apr. 12, 2019", 7 pgs.

* cited by examiner

INSERTABLE CARDIAC MONITORING DEVICE DESIGNED FOR THE MRI ENVIRONMENT

CLAIM OF PRIORITY

This application claims the benefit of priority under 35 U.S.C. § 119(e) of U.S. Provisional Patent Application Ser. No. 62/625,092, filed on Feb. 1, 2018, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be insertable diagnostic-only devices, such as subcutaneously insertable cardiac monitors (ICMs), subcutaneously insertable loop recorders (ILRs), and subcutaneously insertable heart failure monitors (SubQ HFMs). The devices may include electrodes in communication with one or more sense amplifiers to monitor electrical heart activity within a patient, or can include one or more sensors to monitor one or more other physiological parameters of the patient. Subcutaneously implantable devices may include electrodes that are able to sense cardiac signals without being in direct contact with the patient's heart.

Nuclear magnetic resonance imaging (MRI) is a medical imaging technique that can be used to visualize internal structure of the body. MRI is an increasingly common diagnostic tool, therefore, overcoming challenges of operating an ambulatory medical device during an MRI scan or in MRI environments is essential in the design of implantable or insertable medical devices.

Overview

This document describes systems, devices, and methods that can include an implantable or insertable device, (e.g., an ICM, ILR, or SubQ HFM) that is operable in the presence of magnetic resonance imaging (MRI) equipment.

Example 1 includes subject matter (such as an apparatus) comprising a magnetic field detection circuit, a cardiac signal sensing circuit configured to generate a sensed cardiac signal representative of cardiac activity of a subject when coupled to sensing electrodes, a memory circuit, a control circuit, and an arrhythmia detection circuit. The control circuit is configured to store, in the memory circuit, cardiac signal data determined using the sensed cardiac signal, receive an indication of magnetic field detection by the magnetic field detection circuit; and store cardiac signal data determined during the magnetic field detection and store an identifier indicating the magnetic field detection in association with the cardiac signal data. The arrhythmia detection circuit is configured to process the cardiac signal data to detect a cardiac arrhythmia event, and confirm the cardiac arrhythmia event according to the magnetic field indication.

In Example 2, the subject matter of Example 1 optionally includes a plurality of sensing of electrodes operatively coupled to the cardiac signal sensing circuit, wherein the electrodes are configured to be implanted subcutaneously.

In Example 3, the subject matter of one or both of Examples 1 and 2 optionally includes a arrhythmia detection circuit configured to exclude the cardiac signal data determined during the magnetic field detection from the processing by the arrhythmia detection circuit.

In Example 4, the subject matter of one any combination of Examples 1-3 optionally includes a control circuit configured to store the cardiac signal data determined during the magnetic field detection, and delete the stored cardiac signal data determined during magnetic field detection when the cardiac arrhythmia event is not confirmed.

In Example 5, the subject matter of one or any combination of Examples 1-4 optionally include a control circuit configured to identify cardiac signal data determined during a specified duration of time prior to the magnetic field detection, and exclude the identified cardiac signal data from the processing to detect the cardiac arrhythmia event.

In Example 6, the subject matter of one or any combination of Examples 1-5 optionally includes a control circuit configured to identify cardiac signal data determined during a specified duration of time prior to the magnetic field detection; and store the identifier indicating the magnetic field detection in association with the cardiac signal data determined during the specified duration of time.

In Example 7, the subject matter of one or any combination of Examples 1-6 optionally includes a arrhythmia detection circuit configured to detect an episode of atrial fibrillation (AF) using the cardiac signal data; and exclude the cardiac signal data determined during the magnetic field detection from the processing to detect the episode of AF.

In Example 8, the subject matter of one or any combination of Examples 1-7 optionally includes an arrhythmia detection circuit configured to: detect AF using the cardiac signal data; determine AF burden for the subject; and exclude the cardiac signal data determined during the magnetic field detection from the processing to determine the AF burden.

In Example 9, the subject matter of one or any combination of Examples 1-8 optionally includes a physiologic sensing circuit configured to generate a sensed physiologic signal representative of physiology of the subject. The control circuit is optionally configured to: store, in the memory circuit, physiologic data determined using the sensed physiologic signal; and store physiologic data determined during the magnetic field detection and store an identifier indicating the magnetic field detection in association with the physiologic data.

In Example 10, the subject matter of Example 9 optionally includes a physiologic sensing circuit that includes one or more of a heart sound sensing circuit, a thoracic impedance sensing circuit, and a body temperature sensing circuit; and wherein the physiologic signal includes one or more of a heart sound signal representative of one or more heart sounds of the subject, a thoracic impedance signal, and a temperature signal.

In Example 11, the subject matter of one or both of Examples 9 and 10 optionally includes a control circuit configured to identify physiologic data determined during a specified duration of time prior to the magnetic field detection; and store the identifier indicating the magnetic field detection in association with the physiologic data determined during the specified duration of time.

In Example 12, the subject matter of one or any combination of Examples 9-11 optionally includes a heart failure (HF) detection circuit configured to process the physiologic data to detect a change in HF status of the subject; and exclude the physiologic data determined during the magnetic field detection from the processing to detect the change in HF status.

Example 13 includes subject matter (such as a method of operating a medical device, or a computer readable storage medium including instructions that when performed by the medical device cause the medical device to perform the method), or can optionally be combined with one or any combination of Examples 1-12 to include such subject matter, comprising: sensing a cardiac signal representative of cardiac activity of a subject using the medical device; storing cardiac signal data determined using the sensed cardiac signal in a memory circuit of the medical device; receiving an indication of magnetic field detection from a magnetic field detection circuit included in the medical device; storing cardiac signal data determined during the magnetic field detection and storing an identifier indicating the magnetic field detection in association with the cardiac signal data; and detecting a cardiac arrhythmia event using the cardiac signal data and confirming the cardiac arrhythmia event according to the magnetic field indication.

In Example 14, the subject matter of Example 13 optionally includes excluding the physiologic data obtained during the magnetic field detection from the detection of the cardiac arrhythmia event.

In Example 15, the subject matter of one or both of Examples 13 and 14 optionally includes deleting stored data obtained during magnetic field detection when the cardiac arrhythmia event is not confirmed.

In Example 16, the subject matter of one or any combination of Examples 13-15 optionally includes identifying physiologic data obtained during a specified duration of time prior to the magnetic field detection; and excluding the identified physiologic data from the detection of the cardiac arrhythmia event.

In Example 17, the subject matter of one or any combination of Examples 13-16 optionally includes identifying cardiac signal data determined during a specified duration of time prior to the magnetic field detection; and storing the identifier indicating the magnetic field detection in association with the cardiac signal data determined during the specified duration of time.

Example 18 can include subject matter (such as an apparatus), or can optionally be combined with one or any combination of Examples 1-17 to include such subject matter, comprising a magnetic field detection circuit; a cardiac signal sensing circuit configured to generate a cardiac signal representative of cardiac activity of a subject; a plurality of sensing of electrodes operatively coupled to the cardiac signal sensing circuit, wherein the electrodes are configured to be implanted subcutaneously; a memory circuit; and a control circuit operatively coupled to the magnetic field detection circuit, cardiac signal sensing circuit, and memory circuit. The control circuit is configured to: store cardiac signal data determined using the generated cardiac signal in the memory circuit; receive an indication of magnetic field detection by the magnetic field detection circuit; continue to monitor for the magnetic field detection; identify cardiac signal data obtained during a specified duration of time prior to the magnetic field detection; and discard cardiac signal data obtained during a specified duration of time prior to the magnetic field detection and during the magnetic field detection.

In Example 19, the subject matter of Example 18 optionally includes a control circuit configured to store the cardiac signal data determined during the magnetic field detection and determined during the specified duration of time prior to the magnetic field detection, and store an indication of the magnetic field detection with the stored cardiac signal data.

In Example 20, the subject matter of one or both of Examples 18 and 19 optionally includes a control circuit configured to store the cardiac signal data determined during the specified duration of time prior to the magnetic field detection; delete the stored cardiac signal data in response to the indication of magnetic field detection; and exclude from memory storage the cardiac signal data obtained during the magnetic field detection.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
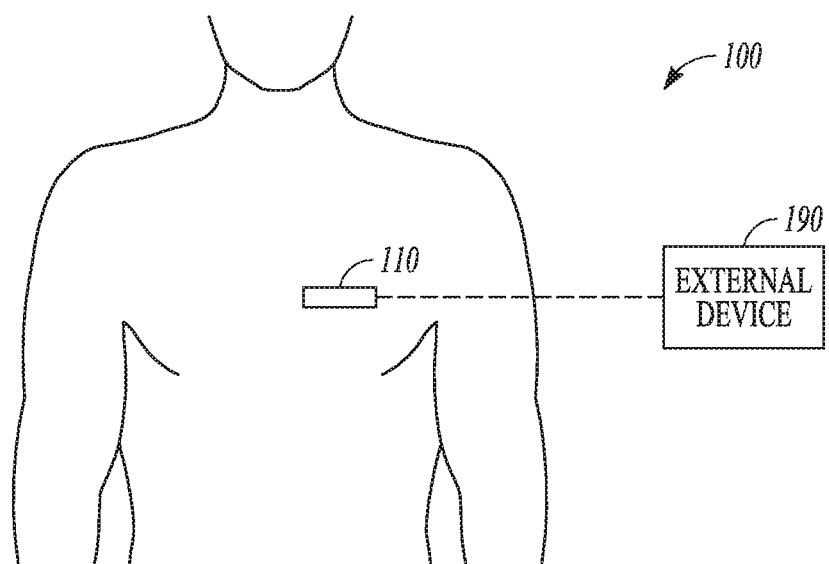
FIG. 1 is an illustration of an example of a system that includes an insertable medical device and an external device.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, in order to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered to alter the alignment of specified nuclei (e.g., within a particular volume or plane to be imaged within the subject). The power, phase, and range of frequencies of the one or more RF excitation pulses can be selected, according to the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during magnetic resonance (MR), to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field can allow a volume or a plane to be imaged more efficiently. In a gradient field example, signals received from relaxing nuclei can include energy in respective unique frequency ranges corresponding to the respective locations of the nuclei.

Active MRI equipment can interfere with operation of an implantable or insertable device. In certain examples, the interference can include disruption in sensing by the device, interference in communication between the device and other implants or external modules during MRI operation, or disruption in monitoring or therapeutic function of the implantable or insertable device.

During an MRI scan, the one or more RF excitation pulses can include energy delivered at frequencies (e.g., from less than 10 MHz to more than 100 MHz) that correspond to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, and can include individual time-varying gradient fields provided in each of the axes to provide imaging in multiple dimensions.

An MR field can create, among other effects, non-physiologic voltages that can cause erroneous sensing of cardiac electrical activity. These effects can make it difficult to sense cardiac events and properly interpret device-obtained physiologic data in the presence a gradient magnetic field, an RF magnetic excitation pulse, or other components of an MR scan (e.g., an active scan). In certain examples, the MR scan can appear to the medical device as intrinsic activity, or can otherwise interfere with physiologic signal detection by the IMD, which can lead to incorrect interpretation of physiologic data obtained by the devices.

FIG. 1 is an illustration of an example of a system 100 that includes an insertable medical device 110 (e.g., a subcutaneously insertable cardiac monitor (ICM), subcutaneously insertable loop recorder (ILR), or subcutaneously insertable heart failure monitor (SubQ HFM)) and an external device 190. The insertable device 110 may be a diagnostic-only device that senses electrical signals of the heart and, depending on the device, other signals of the heart or other physiologic signals. The external device 190 may be a programmer that communicates one or more wireless signals with the insertable device 110, such as by using radio frequency (RF) or by one or more other telemetry methods. The external device 190 can communicate information with the insertable device 110 to configure operation of the insertable device 110 by downloading operating parameters to the insertable device, and to upload data recorded by the insertable device without removal of the device.

Figure 2:
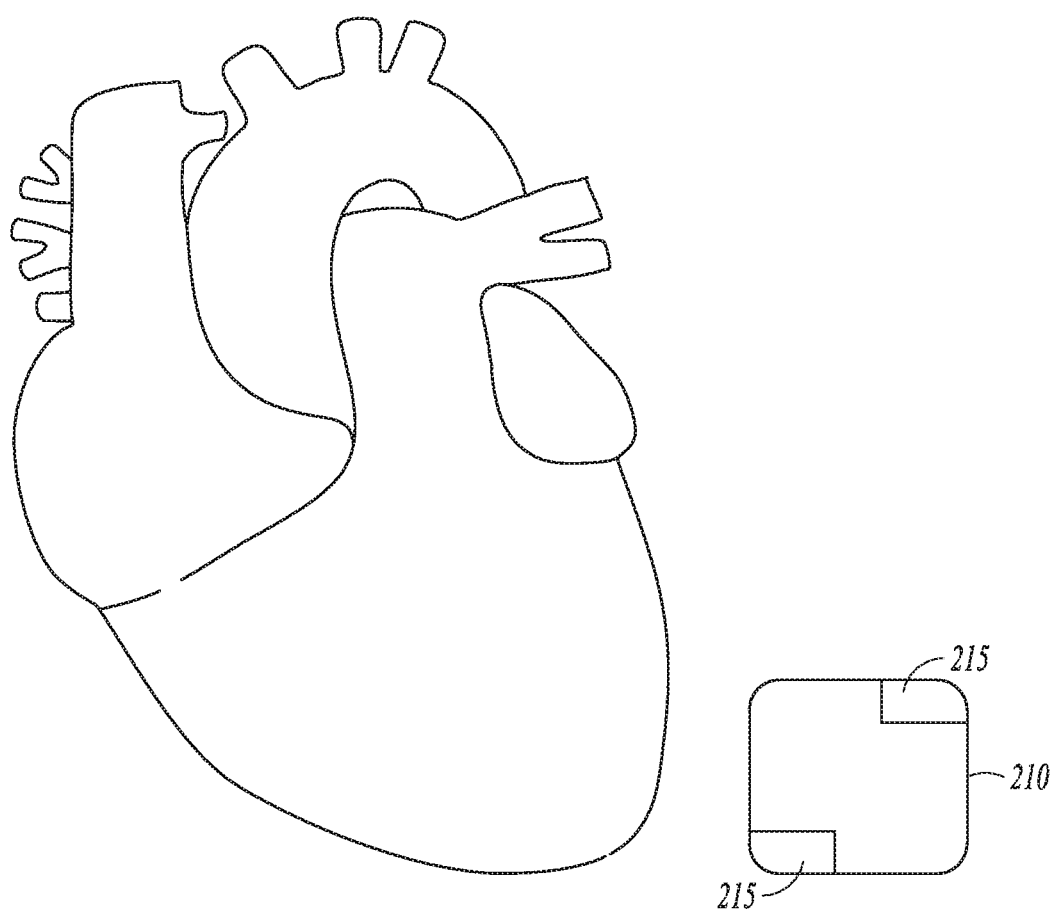
FIG. 2 is an illustration of an example of an insertable medical device

FIG. 2 is an illustration of an example of an insertable medical device 210. The insertable medical device includes a housing that may include a conductive material (e.g., titanium) or may include a non-conductive, non-metallic, non-magnetic material, such as a glass, porcelain, a non-conductive polymer, etc. The insertable medical device 210 may include two or more electrodes 215 on the housing of the device to sense the electrical signals of the heart or other physiologic sensors of the patient or subject. In certain examples, the electrodes are arranged on a subcutaneously implantable or insertable lead in contact with subcutaneous tissues and/or muscle. In some examples, the electrodes are arranged on the device itself.

Subcutaneously insertable devices such as ICMs, ILRs, and SubQ HFMs are useful to monitor specific aspects of the physiology of a patient for extended periods of time while the patient is away from a clinical setting. For example, an ICM may be used to detect episodes of atrial fibrillation (AF) of the patient. The episodes can be totaled or trended to determine an AF burden of the patient. In another example, the subcutaneously insertable devices can be used to monitor progression of heart failure of the patient while the patient is away from a clinical setting.

As explained above, the electromagnetic fields encountered during an MR scan can confound one or more of device-based collecting, storing and interpreting of physiological information. Typically, when a patient that has been prescribed a medical diagnostic device, therapeutic device, or combination device is to undergo an MRI procedure, the operation of the device is altered by a clinician (e.g., a physician) prior to the MRI procedure. For example, the clinician may reprogram the device from a normal operating mode to an MRI-safe mode using a device programmer. After the MRI procedure, the clinician restores the normal mode using the programmer. This adds steps that need to be performed for an MR scan of a patient with a device. It would be desirable to have the medical device to continue to operate during the MRI procedure without a clinician having to change operation of the device by reprogramming the device before and after the procedure.

By having the device itself detect the MRI scanner or MR scan, the device may use information about the MRI procedure to modify how physiological information is obtained, analyzed and displayed, to minimize the possibility of erroneous data and misdiagnosis. This simplifies use of the device for the clinician by eliminating any of the steps typically performed by a clinician in preparation for an MR scan.

Figure 3:
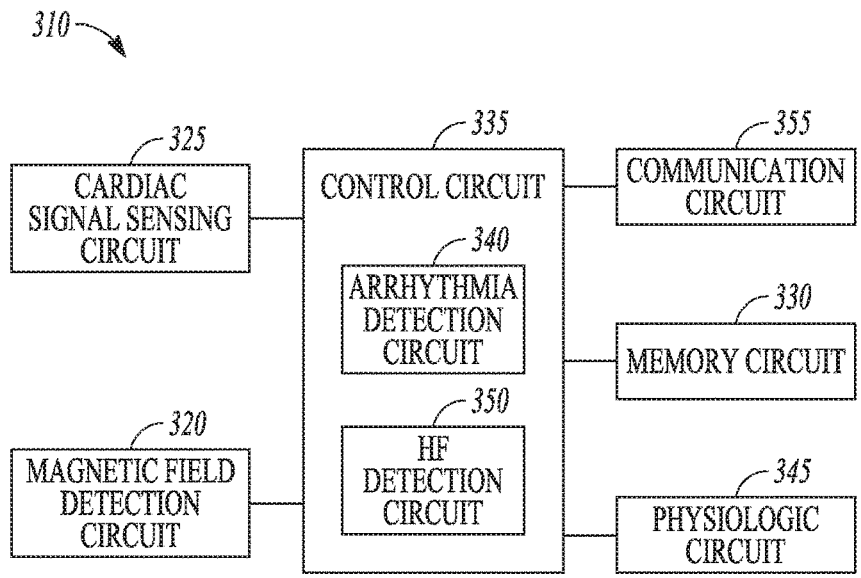
FIG. 3 is a block diagram of portions of an example of an insertable medical device.

FIG. 3 is a block diagram of portions of an example of an insertable medical device 310. The device 310 includes a magnetic field detection circuit 320, a cardiac signal sensing circuit 325, a memory circuit 330, and a control circuit 335. The magnetic field detection circuit can include a static magnetic field sensor (e.g., a Hall Effect sensor, a magnetometer, a reed switch, etc.) configured to detect a static magnetic field. The magnetic field detection circuit can include an active magnetic field sensor (e.g., a transducer, an antenna, a coil, etc.) configured to detect a time-varying gradient magnetic field, a radio frequency magnetic excitation pulse, or one or more other components of an active magnetic field.

The cardiac signal sensing circuit 325 can include one or more sense amplifier circuits (not shown) to produce sensed signals representative of cardiac depolarization of the patient. The sensed cardiac signals can be sampled and stored in the memory circuit 330 as electrograms for later uploading and analysis. The sensed signals can also be used by arrhythmia detection schemes performed by the device. The cardiac signal sensing circuit 325 may generate a cardiac signal representative of cardiac activity of a subject when coupled to sensing electrodes such as the subcutaneously implantable electrodes 215 in FIG. 2.

The control circuit 335 may include one or more of a microprocessor, a digital signal processor, application specific integrated circuit (ASIC), field programmable gate array (FPGA), or other type of processor, interpreting or executing instructions included in software or firmware. The memory circuit 330 may be integral to or separate from the control circuit 335. The control circuit 335 is operatively coupled to the magnetic field detection circuit 320 and the cardiac signal sensing circuit 325, and initiates storage of cardiac signal data obtained using the generated cardiac signal in the memory circuit 330.

When the control circuit receives an indication of magnetic field detection by the magnetic field detection circuit 320, the control circuit 335 modifies its operation to treat the physiological information collected during the presence of the magnetic field differently than when the magnetic field is not detected. When the magnetic field is not detected, the control circuit resumes its normal operation. In certain examples, the indication of magnetic field detection is an electronic signal produced by the magnetic field detection circuit 320 indicating an active state of the magnetic field sensing. The active state of the signal may indicate the presence of a static magnetic field or a time-varying magnetic field.

Figure 4:
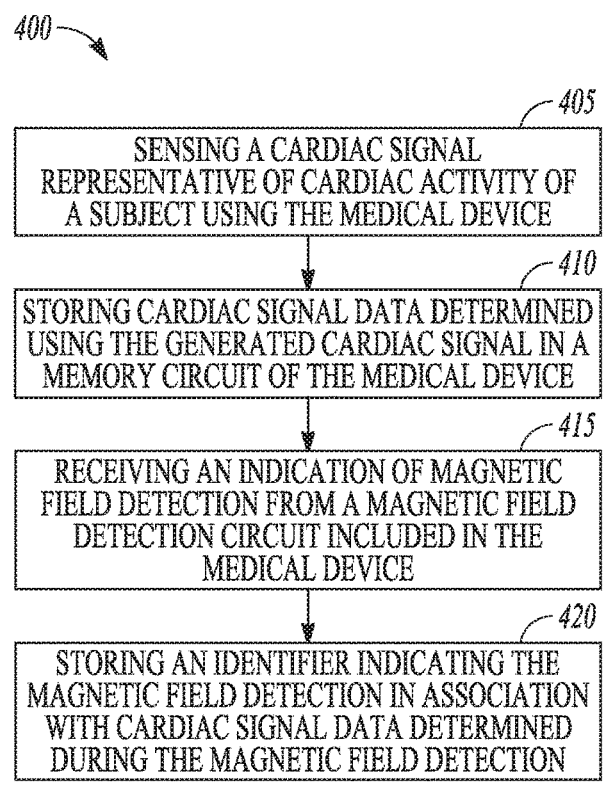
FIG. 4 is a flow diagram of a method of controlling operation of a medical device.

FIG. 4 is a flow diagram of a method of operating or controlling operation of a medical device, such as the insertable medical device 310 of FIG. 3 for example. At 405, a cardiac signal representative of cardiac activity of a subject is sensed using the medical device. At 410, cardiac signal data is determined using the generated cardiac signal is stored in memory circuits of the medical device. In certain examples, the cardiac signal data may include samples of the sensed cardiac signal. In certain examples, the cardiac signal data includes a device-determined interpretation of the cardiac signal data. For instance, the cardiac signal data may include an indication (e.g., a stored digital value, flag, or marker) of an episode of cardiac arrhythmia of the subject.

At 415, an indication of magnetic field detection is received from a magnetic field detection circuit included in the medical device. The magnetic field detection circuit may detect one or both of a static magnetic field and a time-varying magnetic field. At 420, in response to the indication of detection of a magnetic field, the device may continue to collect cardiac signal data, but a control circuit of the device stores an identifier in association with cardiac signal data determined during the magnetic field detection. The identifier indicates the detection of the magnetic field and identifies the data impacted by the magnetic field.

In some examples, after an initial detection of a magnetic field, the control circuit of the device may continue to monitor for the magnetic field detection. The control circuit 335 may identify cardiac signal data obtained during a specified duration of time prior to the magnetic field detection, and discard the cardiac signal data obtained during a specified duration of time prior to the magnetic field detection and during the magnetic field detection. In an example intended to be non-limiting, the control circuit 335 may discard data collected fifteen minutes prior to the initial indication of the magnetic field and the data collected until the magnetic field detection circuit no longer indicates presence of a magnetic field. In some examples, the control circuit 335 doesn't delete the collected data or allow the data to be over written, but stores an identifier indicating the magnetic field detection in association with the cardiac signal data obtained during the specified duration of time.

The insertable device includes a communication circuit 355 that communicates data wirelessly with an external device using RF signals or another wireless telemetry method.

Returning to FIG. 3, the device 310 may include an arrhythmia detection circuit 340. The arrhythmia detection circuit 340 may be included with the control circuit 335 as shown in the example of FIG. 3 or the arrhythmia detection circuit 340 may be a separate circuit. The arrhythmia detection circuit 340 processes the cardiac signal data obtained using the generated cardiac signal to detect a cardiac arrhythmia event. The cardiac arrhythmia event may include, among other things, a bradycardia event, a ventricular tachycardia (VT) event, a ventricular fibrillation (VF) event, and an AF event.

The arrhythmia detection circuit 340 may perform further processing on the data after the detection to confirm that the detected event really was an episode of arrhythmia. For instance, the arrhythmia detection circuit may apply detection criteria having a sensitivity that is more inclusive of detected events as arrhythmia episodes and may apply confirmation criteria having a specificity to be more discriminating in its analysis of the detected events to conclude that the events were arrhythmia episodes.

In an illustrative example intended to be non-limiting, the arrhythmia detection circuit 340 may be an atrial fibrillation (AF) detection circuit. The arrhythmia detection circuit 340 may detect AF when the measured variation between ventricular depolarization intervals (V-V intervals) in the sensed cardiac signal exceeds a specified V-V interval variation threshold. The arrhythmia detection circuit 340 may confirm the AF based on results of a noise analysis of the sensed cardiac signal.

The arrhythmia detection circuit 340 may include the presence of a magnetic field in the criteria for confirming an arrhythmia event. If the magnetic field detection circuit 320 (or stored data) indicates that the cardiac signal data was collected during the detection of a magnetic field, the arrhythmia detection circuit 340 may reject confirmation of the cardiac arrhythmia event based on the magnetic field indication. If the control circuit 335 enables storage of the cardiac signal data determined during the magnetic field detection, the control circuit 335 may delete the stored data obtained during magnetic field detection when the confirmation is rejected by the arrhythmia detection circuit 340.

In some examples, when the magnetic field detection circuit 320 indicates the presence of a magnetic field, the arrhythmia detection circuit 340 excludes the cardiac signal data obtained during the magnetic field detection from the processing performed to detect the cardiac arrhythmia event. For example, the arrhythmia detection circuit 340 may process cardiac signal data obtained using the generated cardiac signal to detect an episode of AF, and exclude the cardiac signal data obtained during the magnetic field detection from the processing to detect the episode of AF.

In some examples, the arrhythmia detection circuit 340 may track episodes of AF to determine the total time that the patient is in AF (this is sometimes referred to as AF burden). The arrhythmia detection circuit 340 may exclude the cardiac signal data obtained during the magnetic field detection from the processing to determine the AF burden. Excluding the cardiac signal data may involve deleting the cardiac signal data, allowing the cardiac signal data to be overwritten, or storing an identifier in association with the cardiac signal data and not using the data associated with the identifier.

The techniques described herein may also be used to monitor other conditions alternatively, or in addition to, cardiac arrhythmia. The insertable device 310 may include one or more other physiologic sensing circuits 345 that produce a physiologic signal used to determine physiologic data for the subject. For instance, the insertable device 310 may be used to monitor the progression of heart failure (HF) of the subject over an extended period of time. The physiologic sensing circuit 345 may include a physiological impedance sensing circuit, such as to measure thoracic impedance of the subject for example. The impedance sensing circuit may include a subcutaneously implantable lead comprising one or more electrodes. One or more electrodes of the lead may be arranged in relation to one or more electrodes of the housing of the insertable device so that a substantial portion of the thorax area of the subject is between the electrodes of the lead and the electrodes of the housing. The insertable medical device may apply a current between the electrodes and measure the resulting voltage to monitor impedance using Ohm's Law.

The thoracic impedance may provide a measure of the amount of fluid in the thorax area of the subject. The thoracic impedance decreases with build-up of fluid from edema. The thoracic impedance can therefore be used to monitor the progression of fluid build-up as one aspect of monitoring heart failure. The insertable device 310 may store thoracic impedance data obtained during the magnetic field detection and store an identifier indicating the magnetic field detection in association with the thoracic impedance data.

In another example, the physiologic sensing circuit 345 can include a heart sound sensing circuit (e.g., an accelerometer, or microphone) that produces an electrical heart sound signal representative of mechanical cardiac activity of the patient or subject. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. The heart sound signal produced by the heart sound sensor circuit can be an electrical signal representative of one or more heart sounds. The insertable device 310 may store heart sound data determined using the heart sound signal during the magnetic field detection and store an identifier indicating the magnetic field detection in association with the heart sound data.

In another example, the physiologic sensing circuit 345 can include a body temperature sensing circuit that produces an electrical temperature signal representative of the body temperature of the patient or subject. The insertable device 310 may store body temperature data determined using the temperature signal during the magnetic field detection and store an identifier indicating the magnetic field detection in association with the body temperature data.

The control circuit 330 may identify physiologic data determined during a specified duration of time prior to the magnetic field detection, and stores the identifier indicating the magnetic field detection in association with the physiologic data determined during the specified duration of time.

The insertable device 310 can include an HF detection circuit 350 that monitors progression of HF status of the subject using one or both of the physiologic data and the cardiac signal data. For instance, the HF detection 350 may monitor the thoracic impedance of the subject and detect a change in HF status of the subject when the thoracic impedance decreases by more than a threshold impedance change. The HF detection may generate an indication of the change by providing an alert signal to the control circuit 335, or by storing an indication in the memory 330. The HF detection circuit may exclude the physiologic data determined during the magnetic field detection from the processing to detect the change in HF status.

According to some examples, the insertable device 310 serves to only collect the data, and the processing to detect a condition of the patient is performed by an external device that uploads the physiologic data from the insertable device. In variations, the insertable device 310 detects the condition of the patient using the physiologic data and the external device confirms the condition using the uploaded physiologic data. For example, the external device in FIG. 1 may process cardiac signal data uploaded from the insertable device 310 for one or both of detecting cardiac arrhythmia and confirming cardiac arrhythmia. In some examples, the external device 190 uploads the data from the insertable device 310 and transmits the data to a third device (e.g., a remote server) that processes the cardiac signal data.

In some examples, the insertable device 310 discards the physiologic data collected in the presence of the magnetic field by deleting the data or allowing the data to be overwritten, and the external device never receives the physiologic data that may be suspect due to the presence of the magnetic field. In some examples, the physiologic data uploaded from the insertable device 310 includes the physiologic data collected in the presence of the magnetic field, but the data includes an identifier to identify the suspect data. The external device (e.g., either external programmer or server) decides whether to use the suspect data in the processing of the physiologic data to detect or confirm a physiological event.

Subcutaneously insertable devices are useful to collect physiological information of a patient for extended periods of time while the patient is away from a clinical setting. The devices, systems and methods described herein allow for operation of the insertable device during an MR scan by managing the physiological data collected by the device during the MR scan. This eliminates the need for a clinician to perform steps to reconfigure an insertable device for an MR scan.

Additional Description

The systems, devices, and methods discussed in this document may improve the medical technology of automated cardiac rhythm management (CRM) and detection and prevention of worsening of cardiac function. The heart rate-based arrhythmia detection may also enhance the performance and functionality of an implantable CRM device, in certain examples, increasing the efficacy of existing AF detection (e.g., by detecting the true onset of AF), such that system performance can be improved with little to no additional cost, while reducing manual inspection required for such detection. In other examples, existing system performance can be maintained (e.g., high AF sensitivity and specificity, etc.) using lower cost or less obtrusive systems, apparatus, and methods. For example, because the system or device does not require direct atrial activity sensing for atrial arrhythmias detection, the system complexity and implementation cost may be reduced. It may particularly be beneficial for patient not indicated for atrial lead implantation either for atrial activity sensing or for atrial pacing. The device-based arrhythmia detection also allows for more efficient use of device memory, such as by correctly storing heart rate statistics that are clinically relevant to arrhythmia recognition. Because onset of AF is more accurately reported, fewer unnecessary drugs and procedures can be scheduled, prescribed, or provided, and the overall management of the patient's cardiac disease can be improved.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a magnetic field detection circuit;
   a cardiac signal sensing circuit configured to generate a sensed cardiac signal representative of cardiac activity of a subject when coupled to sensing electrodes;
   a memory circuit;
   a control circuit operatively coupled to the magnetic field detection circuit; the cardiac signal sensing circuit, and the memory circuit, and configured to:
      store, in the memory circuit, cardiac signal data determined using the sensed cardiac signal;
      receive an indication of magnetic field detection by the magnetic field detection circuit; and
      store cardiac signal data determined during the magnetic field detection and store an identifier indicating the magnetic field detection in association with the cardiac signal data; and
   an arrhythmia detection circuit configured to process the cardiac signal data to detect a cardiac arrhythmia event; and confirm the cardiac arrhythmia event according to the magnetic field indication.

2. The apparatus of claim 1, including a plurality of sensing of electrodes operatively coupled to the cardiac signal sensing circuit, wherein the electrodes are configured to be implanted subcutaneously.

3. The apparatus of claim 1, wherein the arrhythmia detection circuit is configured to exclude the cardiac signal data determined during the magnetic field detection from the processing by the arrhythmia detection circuit.

4. The apparatus of claim 1, wherein the control circuit is configured to store the cardiac signal data determined during the magnetic field detection, and delete the stored cardiac signal data determined during magnetic field detection when the cardiac arrhythmia event is not confirmed.

5. The apparatus of claim 4, wherein the control circuit is configured to identify cardiac signal data determined during a specified duration of time prior to the magnetic field detection, and exclude the identified cardiac signal data from the processing to detect the cardiac arrhythmia event.

6. The apparatus of claim 1, wherein the control circuit is configured to identify cardiac signal data determined during a specified duration of time prior to the magnetic field detection; and store the identifier indicating the magnetic field detection in association with the cardiac signal data determined during the specified duration of time.

7. The apparatus of claim 1, wherein the arrhythmia detection circuit is configured to detect an episode of atrial fibrillation (AF) using the cardiac signal data; and exclude the cardiac signal data determined during the magnetic field detection from the processing to detect the episode of AF.

8. The apparatus of claim 1, wherein the arrhythmia detection circuit is configured to:
   detect AF using the cardiac signal data;
   determine AF burden for the subject; and exclude the cardiac signal data determined during the magnetic field detection from the processing to determine the AF burden.

9. The apparatus of claim 1, including:
a physiologic sensing circuit configured to generate a sensed physiologic signal representative of physiology of the subject;
wherein the control circuit is configured to:
    store, in the memory circuit, physiologic data determined using the sensed physiologic signal; and
    store physiologic data determined during the magnetic field detection and store an identifier indicating the magnetic field detection in association with the physiologic data.

10. The apparatus of claim 9, wherein the physiologic sensing circuit includes one or more of a heart sound sensing circuit, a thoracic impedance sensing circuit, and a body temperature sensing circuit; and wherein the physiologic signal includes one or more of a heart sound signal representative of one or more heart sounds of the subject, a thoracic impedance signal, and a temperature signal.

11. The apparatus of claim 9, wherein the control circuit is configured to identify physiologic data determined during a specified duration of time prior to the magnetic field detection; and store the identifier indicating the magnetic field detection in association with the physiologic data determined during the specified duration of time.

12. The apparatus of claim 9, including a heart failure (HF) detection circuit configured to process the physiologic data to detect a change in HF status of the subject; and exclude the physiologic data determined during the magnetic field detection from the processing to detect the change in HF status.

13. A method of operating a medical device, the method comprising:

sensing a cardiac signal representative of cardiac activity of a subject using sensing electrodes of the medical device;
storing cardiac signal data determined using the sensed cardiac signal in a memory circuit of the medical device;
receiving an indication of magnetic field detection from a magnetic field detection circuit included in the medical device;
storing cardiac signal data determined during the magnetic field detection and storing an identifier indicating the magnetic field detection in association with the cardiac signal data; and
detecting a cardiac arrhythmia event using the cardiac signal data and confirming the cardiac arrhythmia event according to the magnetic field indication.

14. The method of claim 13, including excluding the cardiac signal data obtained during the magnetic field detection from the detection of the cardiac arrhythmia event.

15. The method of claim 13, including deleting stored data obtained during magnetic field detection when the cardiac arrhythmia event is not confirmed.

16. The method of claim 13, including identifying cardiac signal data obtained during a specified duration of time prior to the magnetic field detection; and excluding the identified cardiac signal data from the detection of the cardiac arrhythmia event.

17. The method of claim 16, including identifying cardiac signal data determined during a specified duration of time prior to the magnetic field detection; and storing the identifier indicating the magnetic field detection in association with the cardiac signal data determined during the specified duration of time.

* * * * *